United States Patent
Pan et al.

(10) Patent No.: US 10,456,343 B2
(45) Date of Patent: Oct. 29, 2019

(54) MICROEMULSION COMPOSITIONS COMPRISING POLYDATIN AND METHOD OF USE

(71) Applicant: L'OREAL, Paris (FR)

(72) Inventors: Zhi Pan, Ridgewood, NJ (US); Yan Yu, ShangHai (CN); Anne-Laure Suzanne Bernard, NY, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/416,781

(22) Filed: Jan. 26, 2017

(65) Prior Publication Data

US 2018/0207077 A1 Jul. 26, 2018

(51) Int. Cl.
| | | |
|---|---|---|
| *A61K 8/60* | (2006.01) | |
| *A61K 8/06* | (2006.01) | |
| *A61K 8/67* | (2006.01) | |
| *A61K 8/85* | (2006.01) | |
| *A61K 8/41* | (2006.01) | |
| *A61K 8/92* | (2006.01) | |
| *A61K 8/34* | (2006.01) | |
| *A61K 8/46* | (2006.01) | |
| *A61Q 19/00* | (2006.01) | |

(52) U.S. Cl.
CPC ............... *A61K 8/60* (2013.01); *A61K 8/068* (2013.01); *A61K 8/602* (2013.01); *A61K 8/675* (2013.01); *A61Q 19/00* (2013.01)

(58) Field of Classification Search
CPC .......... A61K 2800/21; A61K 2800/262; A61K 2800/48; A61K 8/06; A61K 8/068; A61K 8/37; A61K 8/375; A61K 8/4953; A61K 8/673; A61K 8/675; A61Q 19/00; A61Q 19/10; A61Q 1/00; A61Q 1/14
See application file for complete search history.

(56) References Cited

U.S. PATENT DOCUMENTS

| | | | |
|---|---|---|---|
| 5,773,014 A | 6/1998 | Perrier et al. | |
| 6,414,037 B1 * | 7/2002 | Pezzuto | A61K 8/347 |
| | | | 514/733 |
| 7,763,288 B2 | 7/2010 | Sovak et al. | |
| 7,772,444 B2 | 8/2010 | Huang et al. | |
| 7,776,915 B2 | 8/2010 | Morariu | |
| 8,568,804 B2 | 10/2013 | Fisher et al. | |
| 8,828,458 B2 | 9/2014 | Morariu | |
| 2006/0269494 A1 | 11/2006 | Gupta | |
| 2008/0035242 A1 | 2/2008 | Maes et al. | |
| 2011/0268812 A1 | 9/2011 | Cauchard et al. | |
| 2012/0201865 A1 | 8/2012 | Doralraju et al. | |
| 2014/0018437 A1 | 1/2014 | Taylor et al. | |
| 2015/0005247 A1 * | 1/2015 | Chen | A61K 8/347 |
| | | | 514/27 |
| 2015/0335560 A1 * | 11/2015 | Bernard | A61K 8/37 |
| | | | 424/401 |
| 2016/0038611 A1 | 2/2016 | Vile et al. | |
| 2017/0281505 A1 | 10/2017 | Pan et al. | |

FOREIGN PATENT DOCUMENTS

| | | |
|---|---|---|
| CN | 101357114 A | 2/2009 |
| CN | 102258434 A | 11/2011 |
| CN | 103251516 A | 8/2013 |
| CN | 104622741 A | 5/2015 |
| CN | 104688624 A | 6/2015 |
| CN | 105287286 A | 2/2016 |
| CN | 105310906 A | 2/2016 |
| CN | 105769604 A | 7/2016 |
| CN | 105997633 A | 10/2016 |
| EP | 1616551 A1 | 1/2006 |
| EP | 2087894 A1 | 8/2009 |
| EP | 2674155 A1 | 12/2013 |
| FR | 2844714 A1 | 3/2004 |
| FR | 2844715 A | 3/2004 |
| FR | 2862533 B | 5/2005 |
| FR | 2867977 A | 9/2005 |
| FR | 2873024 A | 1/2006 |
| FR | 2905862 A | 3/2008 |
| FR | 2906139 A | 3/2008 |
| FR | 2906143 B | 3/2008 |
| FR | 2918887 B | 1/2009 |
| FR | 2958845 A1 | 10/2011 |
| JP | 2010024208 A | 2/2010 |
| JP | 2013216650 A | 10/2013 |
| JP | 2013241399 A | 12/2013 |
| JP | 2014171436 A | 9/2014 |
| KR | 20110068258 A | 6/2011 |
| KR | 20120136141 A | 12/2012 |
| KR | 20130050553 A | 5/2013 |
| KR | 20130115971 A | 10/2013 |
| KR | 20140081272 A | 7/2014 |
| KR | 20140103576 A | 8/2014 |

(Continued)

OTHER PUBLICATIONS

Atrux-Tallau N, et al., Quantitative analysis of ligand effects on bioefficacy of nanoemulsion encapsulating depigmenting active, Colloids Surf B Biointerfaces. Oct. 1, 2014;122:390-395.
Ju Jin, et al., "Evaluation of Both Free Radical Scavenging Capacity and Antioxidative Damage Effect of Polydatin," Adv Exp Med Biol. 2016;923:57-62.
Jeong ET, et al., "Inhibition of melanogenesis by piceid isolated from Polygonum cuspidatum," Arch Pharm Res. Sep. 2010; 33(9):1331-8.
Deep Waters Nutrient Hydrator, Clinical Skin Care Products, Unfading Beauty.
International Search Report and Written Opinion dated Mar. 29, 2018 in corresponding PCT Application No. PCT/US18/14936.

*Primary Examiner* — Anna R Falkowitz
(74) *Attorney, Agent, or Firm* — Polsinelli PC

(57) ABSTRACT

The instant disclosure relates to microemulsion compositions comprising polydatin, which are useful as cosmetic and/or pharmaceutical compositions for application to the skin and/or hair. The microemulsion compositions comprise: (a) polydatin; (b) optionally, niacinamide; (c) optionally, baicalin; (d) one or more oils; (e) water; and (f) one or more emulsifiers. Furthermore, the ratio of the total amount of the one or more emulsifiers to the total amount of the one or more oils is typically 1.7 to 2.5.

16 Claims, No Drawings

(56) References Cited

FOREIGN PATENT DOCUMENTS

| | | |
|---|---|---|
| KR | 20140143005 A | 12/2014 |
| KR | 20150012785 A | 2/2015 |
| KR | 20150066807 A | 6/2015 |
| KR | 20160019855 A | 2/2016 |
| KR | 20160031850 A | 3/2016 |
| KR | 20160057189 A | 5/2016 |
| KR | 20160057248 A | 5/2016 |
| KR | 20160065328 A | 6/2016 |
| WO | WO-2007104867 A2 | 9/2007 |
| WO | WO-2009129627 A1 | 10/2009 |
| WO | WO-2012131623 A2 | 10/2012 |
| WO | WO-2013019049 A1 | 2/2013 |
| WO | WO-2015082427 A1 | 6/2015 |
| WO | WO-2015156328 A1 | 10/2015 |

\* cited by examiner

MICROEMULSION COMPOSITIONS COMPRISING POLYDATIN AND METHOD OF USE

FIELD OF THE DISCLOSURE

The instant disclosure relates to microemulsion compositions comprising polydatin, which are useful as cosmetic and/or pharmaceutical compositions. Methods for making and using the microemulsion compositions are also disclosed.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

Oxidative stress causes an increase in inflammation, a decrease in collagen levels, overexpression of the enzyme MMP, an increase in protein glycation, and an increase in mitochondrial decay throughout the skin. Additional aging processes include the intrinsic rate of proton leakage across the inner mitochondrial membrane, decreased membrane fluidity, and decreased levels and function of cardiolipin. The mitochondria, which create the energy the cells need by converting dietary and other cellular fuels into ATP, are adversely affected by these aging processes. It has been shown that oxidants generated by mitochondria are the major source of the oxidative lesions in the mitochondria that accumulate with age. (Ames B N, et al., Biochim Biophys Acta. 1995 May 24; 1271(1):165-70). In older skin, the mitochondria become severely impaired, and this leads to both a decrease in ATP production and greater oxidative damage.

Antioxidants are useful agents treating the skin from damage caused by chronoaging and photoaging. Useful antioxidants include those that provide the highest capacity to absorb free radicals. The oxygen radical absorbance capacity (ORAC) is a measurement of a materials ability to absorb free radicals (Dreher F, Maibach H. Curr Probl Dermatol. 2001; 29:157-64.). Antioxidants destroy harmful oxygen free radicals. Examples of Antioxidants include vitamins E, C, D, A, ferulic acid, neohesperidin dihydrochalcone, glutathione, melatonin, metallic zinc, beta-carotene, and numerous other compounds. Antioxidants scavenge oxidation of cells caused by oxygen free radicals, thereby preventing cell damage, and in turn protect the skin.

SUMMARY OF THE DISCLOSURE

The microemulsion compositions disclosed herein comprise polydatin. Polydatin (3,4',5-trihydroxystibene-3-β-mono-D glucoside), which is also called piceid, is a stilbene compound that can be extracted from the root and rhizome of *Polygonum cuspidatum*. It is an antioxidant that is beneficial to the skin. For example, it imparts anti-inflammation and photoprotective properties, which help skin maintain a healthy, youthful, and radiant appearance. The clinical use of polydatin, however, has been limited due to its extremely low water solubility and limited skin-penetration capacity.

The inventors of the instant disclosure discovered that the incorporation of polydatin into the microemulsion compositions disclosed herein results in a variety of surprising and unexpected results. For example, polydatin is solubilized in the microemulsion compositions up to about 1.5%, which is 150 times the solubility of polydatin in water alone. A higher amount of solubilized polydatin is particularly beneficial in cosmetic compositions for application to the skin because it allows for increased transdermal delivery. The inventors also unexpectedly discovered that polydatin acts as a "clarifying agent," i.e., it improves or enhances the transparency (clarity) of microemulsion compositions.

The microemulsion compositions typically include:
 (a) polydatin;
 (b) optionally, niacinamide;
 (c) optionally, baicalin;
 (d) one or more oils;
 (e) water; and
 (f) one or more emulsifiers.

Further, the ratio of the total amount of the one or more emulsifiers to the total amount of the one or more oils is typically from 1.7 to 2.5.

The microemulsion compositions are particularly useful for application to the skin, for example, as cosmetic or pharmaceutical compositions. Thus, the instant disclosure relates to methods for using the microemulsion compositions for cosmetic or pharmaceutical purposes. For example, the disclosure relates to methods for improving the appearance of skin and hair by applying a microemulsion composition described herein to the skin or hair. Additionally, methods for improving or increasing the solubility of polydatin, methods for enhancing the skin penetration, and methods for providing full spectrum photo-protection as also disclosed.

DETAILED DESCRIPTION OF THE DISCLOSURE

The microemulsion compositions of the instant disclosure are unique in how they solubilize and deliver polydatin. The microemulsion compositions include: (a) polydatin; (b) optionally, niacinamide; (c) optionally, baicalin; (d) one or more oils; (e) water; and (f) one or more emulsifiers. Typically, the ratio of the total amount of the one or more emulsifiers to the total amount of the one or more oils is 1.7 to 2.5.

The amount of polydatin in the microemulsion compositions is typically from 0.1 to 5 wt. % of polydatin, based on the total weight of the microemulsion composition. The total amount of polydatin in a microemulsion composition can further be, for example, 0.1 to 4 wt. %, 0.1 to 3 wt. %, 0.5 to 2 wt. %, 0.5 to 5 wt. %, 0.5 to 4 wt. %, 0.5 to 3 wt. %, or 0.5 to 2 wt. %.

The microemulsion compositions of the instant disclosure may optionally include niacinamide, also known as nicotinamide, which is the amide of nicotinic acid (vitamin $B_3$/niacin). The amount of niacinamide in the microemulsion compositions, if present, is typically from 0.1 to 10 wt. %, based on the total weight of the microemulsion composition. Further, the total amount of niacinamide in a microemulsion composition can be 0.1 to 8 wt. %, 0.1 to 6 wt. %, 0.1 to 5 wt. %, 0.1 to 4 wt. %, 0.1 to 3 wt. %, 0.5 to 10 wt. %, 0.5 to 8 wt. %, 0.5 to 6 wt. %, 0.5 to 5 wt. %, 0.5 to 4 wt. %, 0.5 to 3 wt. %, 1 to 10 wt. %, 1 to 8 wt. %, 1 to 6 wt. %, 1 to 5 wt. %, 1 to 4 wt. %, or 1 to 3 wt. %.

The microemulsion compositions of the instant disclosure may optionally include baicalin. Baicalin is a flavone glycoside (it is the glucuronide of baicalein) and is found in several species in the genus *Scutellaria*, including *Scutellaria baicalensis* and *Scutellaria lateriflora*. The amount of baicalin in the microemulsion compositions, if present, is typically in an amount of 0.1 to 3 wt. %, based on the total weight of the microemulsion composition. Further, the total amount of baicalin in a microemulsion compositions can be 0.1 to 2.5 wt. %, 0.1 to 2 wt. %, 0.1 to 1.5 wt. %, 0.1 to 1 wt. %, 0.1 to 0.8 wt. %, 0.1 to 0.5 wt. %, 0.2 to 3 wt. %, 0.2 to 2 wt. %, 0.2 to 1.5 wt. %, 0.2 to 1 wt. %, 0.2 to 0.8 wt. %, 0.2 to 0.5 wt. %, or 0.2 to 0.8 wt. %.

The microemulsion compositions include one or more emulsifiers. Many emulsifiers are known in the art and can be used in the microemulsion compositions. In some cases, the one or more emulsifiers may be selected from the group consisting polygylcerol esters of fatty acids, alkyl polyglycosides, polysorbates, amino acid emulsifiers, and an alkyl amine oxides.

The total amount of the one or more emulsifiers in the microemulsion compositions is typically from 0.5 to 10 wt. %, based on the total weight of the microemulsion composition. Further, the total amount of one or more emulsifiers in a microemulsion composition can be from 0.5 to 8 wt. %, 0.5 to 6 wt. %, 0.5 to 5 wt. %, 1 to 10 wt. %, 1 to 8 wt. %, 1 to 6 wt. %, 1 to 5 wt. %, 2 to 10 wt. %, 2 to 8 wt. %, 2 to 6 wt. %, 2 to 5 wt. %, 3 to 10 wt. %, 3 to 8 wt. %, 3 to 6 wt. %, or 3 to 5 wt. %.

The one or more emulsifiers may include one or more polyglycerol esters of fatty acids, such as, for example, nonionic polyglycerol esters of fatty acids. Non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

The total amount of the one or more non-ethoxylated nonionic polyglycerol esters of fatty acids in the microemulsion compositions is typically from 0.5 to 10 wt. %, based on the total weight of the microemulsion composition. Further, the total amount of non-ethoxylated nonionic polyglycerol esters of fatty acids in a microemulsion composition can be from 0.5 to 8 wt. %, 0.5 to 6 wt. %, 0.5 to 5 wt. %, 1 to 10 wt. %, 1 to 8 wt. %, 1 to 6 wt. %, 1 to 5 wt. %, 2 to 10 wt. %, 2 to 8 wt. %, 2 to 6 wt. %, 2 to 5 wt. %, 3 to 10 wt. %, 3 to 8 wt. %, 3 to 6 wt. %, or 3 to 5 wt. %.

The one or more emulsifiers may include one or more amino acid emulsifiers. Non-limiting examples of amino acid emulsifiers include potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine palmitoyl glycine, sodium lauroyl glycine, sodium cocoyl glycine, sodium myristoyl glycine, potassium lauroyl glycine, potassium cocoyl glycine, potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof.

Mention is also made of potassium lauroyl sarcosinate, potassium cocoyl sarcosinate, sodium cocoyl sarcosinate, sodium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

In some cases, the one or more amino acid emulsifiers can be selected from the group consisting of sodium methyl oleoyl taurate, sodium methyl stearoyl taurate, sodium methyl palmitoyl taurate, sodium methyl myristoyl taurate, sodium methyl lauroyl taurate, sodium methyl cocoyl taurate, and mixtures thereof.

The total amount of the one or more amino acid emulsifiers in the microemulsion compositions is typically from 0.01 to 5 wt. %, based on the total weight of the microemulsion composition. Further, the total amount of amino acid emulsifiers can be from 0.01 to 4 wt. %, 0.01 to 3 wt. %, 0.01 to 2 wt. %, 0.01 to 1 wt. %, 0.05 to 4 wt. %, 0.05 to 3 wt. %, 0.05 to 2 wt. %, 0.05 to 1 wt. %, or 0.05 to 0.5 wt. %

Particular combinations of emulsifiers may be used in the microemulsion compositions. For example, a combination of one or more polygylcerol esters of fatty acids and one or more amino acid emulsifiers may be used. Thus, in some cases, the instant disclosure relates to microemulsion compositions comprising a combination of two or more emulsifiers. For example, the disclosure relates to an emulsifier combination that includes at least one polygylcerol ester of fatty acid. Likewise, the disclosure relates to an emulsifier combination that includes at least one amino acid emulsifier. Further the disclosure relates to an emulsifier combination that includes at least one alkyl polyglycoside, or at least one polysorbate, or at least one alkyl amine oxide. In some cases a combination of at least one polygylcerol ester of fatty acid and at least one amino acid emulsifier (e.g., polyglyceryl-5 laurate and sodium methyl stearoyl taurate) is used.

The weight ratio of the polyglyceryl fatty acid ester to the oil may be from 0.3 to 6, from 0.4 to 3, from 1.7 to 2.5, or from 0.5 to 1.5.

The microemulsion compositions include one or more oils. Typically, the total amount of the one or more oils in the microemulsion compositions is 0.5 to 15 wt. %, based on the total weight of the microemulsion composition. Likewise, the total amount of the one or more oils may be 0.5 to 12 wt. %, 0.5 to 10 wt. %, 0.5 to 8 wt. %, 0.5 to 6 wt. %, 0.5 to 5 wt. %, 0.5 to 4 wt. %, or 0.5 to 3 wt %, based on the total weight of the microemulsion composition. Moreover, the total amount of the one or more oils may be 1 to 15 wt. %, 1 to 12 wt. %, 1 to 10 wt. %, 1 to 8 wt. %, 1 to 6 wt. %, 1 to 5 wt. %, 1 to 4 wt. % or 1 to 3 wt. %.

The one or more oils may be, for example, mineral-based oils, petroleum-based oils, plant-based oils, animal-based oils, and/or synthetic oils. In some cases, the microemulsion compositions include one or more ester oils obtained from a $C_{12}$-$C_{22}$ linear fatty acid and a $C_6$-$C_{24}$ linear or branched alcohol. Non-limiting examples of ester oils include hexyl laurate, myristyl myristate, cetyl myristate, cetyl palmitate, stearyl stearate, decyl oleate, oleyl oleate, cetyl ricinoleate, isocetyl myristate, isostearyl myristate, octyldodecyl myristate, 2-ethylhexyl palm itate, isocetyl palm itate, isostearyl palm itate, 2-ethylhexyl stearate, isocetyl stearate, isodecyl oleate, octyldodecyl oleate, octyldodecyl ricinoleate, and mixtures thereof.

Typically, the total amount of water in the microemulsion compositions is 50 to 85 wt. %, based on the total weight of the microemulsion composition. Further, the total amount of water may be 50 to 80 wt. %, 50 to 75 wt. %, 50 to 70 wt. %, 55 to 85 wt. %, 55 to 80 wt. %, 55 to 75 wt. %, 55 to 70 wt. %, 60 to 85 wt. %, 60 to 80 wt. %, 60 to 75 wt. %, or 60 to 70 wt. %.

The water is often part of a cosmetically acceptable carrier, which may comprise water soluble components. The cosmetically acceptable carrier can include, for example, glycerin, $C_{1-4}$ alcohols, organic solvents, polyols, glycols, and combinations thereof. The total amount of the cosmetically acceptable carrier (which includes the amounts of water discussed above) in the microemulsion compositions may be 50 to 96 wt. %, based on the total weight of the microemulsion composition. Further, the total amount of the cosmetically acceptable carrier may be 50 to 95 wt. %, 50 to 92 wt. %, 50 to 90 wt. %, 50 to 85 wt. %, 50 to 80 wt. %, 55 to 95 wt. %, 55 to 92 wt. %, 55 to 90 wt. %, 55 to 85 wt. %, 55 to 80 wt. %, 60 to 95 wt. %, 60 to 92 wt. %, 60 to 90 wt. %, 60 to 85 wt. %, or 60 to 80 wt. %.

In some cases, the cosmetically acceptable carrier (and therefore the microemulsion compositions) includes one or more glycols. For example, the one or more glycols can include ethylene glycol, propylene glycol, butylene glycol, caprylyl glycol, hexylene glycol, dipropylene glycol, and diethylene glycol. The total amount of the one or more glycols, if present, may be 5 to 40 wt. %, 5 to 35 wt. %, 5 to 30 wt. %, 5 to 25 wt. %, 5 to 20 wt. %, 10 to 40 wt. %, 10 to 35 wt. %, 10 to 30 wt. %, 10 to 25 wt. %, 10 to 20 wt. %, 15 to 40 wt. %, 15 to 35 wt. %, 15 to 30 wt. %, 15 to 25 wt. %, 15 to 20 wt. %, 20 to 40 wt. %, 20 to 35 wt. %, or 20 to 30 wt. %, based on the total weight of the microemulsion composition.

In some cases, the microemulsion compositions of the instant disclosure are transparent or clear. The terms "transparent" and "clear" are used here interchangeably to mean that the composition allows 70% of visible light (400-700 nm) to pass through when measured using a commercial spectrophotometer. To confirm the clarity of the instant composition, a Cary500 UV-Vis-NIR spectrophotometer and disposable UV-cuvete (12.5×12.5×45 mm) were initially used. Subsequently, the compositions could be assessed visually and confirmed to remain clear. The clarity and stability of the formulations did not change for at least 2-months of monitoring.

The microemulsion compositions of the instant disclosure, in some instances, provide full spectrum photo-protection to hair or skin. Accordingly, the instant disclosure relates to methods of providing full spectrum photo-protection to skin or hair comprising applying a microemulsion composition as described herein to the skin or hair. The term "full spectrum photo protection" refers to protection against at least UV radiation and to protection against visible light and/or IR ration. In some cases, the microemulsion compositions may include one or more UV filters.

The instant disclosure further relates to methods for improving the appearance of skin and/or methods for enhancing the skin penetration of polydatin, the methods comprising applying the microemulsion compositions described herein to the skin. Additionally, the disclosure relates to methods for enhancing the solubility of polydatin, for example, in cosmetic or pharmaceutical compositions, comprising incorporating polydatin into a microemulsion such that the microemulsion comprises: (a) polydatin; (b) optionally, niacinamide; (c) optionally, baicalin; (d) one or more oils; (e) water; and (f) one or more surfactants; wherein each component can be further defined as set forth above.

More exhaustive but non-limiting lists of components useful in the microemulsion compositions are presented below.

Oils

The one or more oils typically include those generally used in cosmetics and particularly from oils of animal, vegetable or mineral origin, linear or branched hydrocarbons, optionally branched and/or unsaturated fatty acids, optionally branched and/or unsaturated fatty alcohols, mono- and/or polyesters of fatty acids and/or of fatty alcohols, perfluorinated and/or organofluorinated oils, volatile or non-volatile silicone oils, fluorosilicone oils and their mixtures.

Non-limiting examples of oils include oils of animal, vegetable or mineral origin, of lanolin, squalene, fish oil, perhydrosqualene, mink oil, turtle oil, soybean oil, grape seed oil, sesame oil, maize oil, rapeseed oil, sunflower oil, cottonseed oil, avocado oil, olive oil, castor seed oil, jojoba seed oil, peanut oil, sweet almond oil, palm oil, cucumber oil, hazelnut oil, apricot kernel oil, wheat germ oil, calophyllum oil, macadamia oil, coconut oil, cereal germ oil, candlenut oil, thistle oil, candelilla oil, safflower oil, shea butter, and their mixtures.

Mention is made, as an example of linear or branched hydrocarbons, of oils of mineral or synthetic origin, such as liquid paraffins and their derivatives, petrolatum, mineral oils, (mixtures of oil-derived hydrocarbon oils), polybutene, hydrogenated polyisobutene, polyisoprene, polydecenes such as hydrogenated polydecene, or also linear, branched and/or cyclic alkanes which are optionally volatile, such as, for example, isohexadecane, isododecane, isodecane or isohexadecane, and their mixtures.

Mention is made, as examples of optionally branched and/or unsaturated fatty acids, of myristic acid, palmitic acid, stearic acid, behenic acid, oleic acid, linoleic acid, linolenic acid or isostearic acid, and their mixtures.

Mention is made, as example of optionally branched and/or unsaturated fatty alcohols, of cetanol, stearyl alcohol, oleyl alcohol, cetyl alcohol, octyldodecanol, and their mixtures.

Mention is made, as examples of esters, of monoesters or polyesters of fatty acids, the linear or branched fatty chain of which includes from 6 to 30 carbon atoms, and of fatty alcohols, the fatty chain of which includes from 3 to 30 carbon atoms, in particular mono- and polyesters of hydroxy acids and of fatty alcohols, esters of benzoic acid and of fatty alcohols, polyesters of polyols, dipentaerythrityl $C_5$-$C_9$ esters, trimethylolpropane polyesters, propylene glycol polyesters, polyesters of hydrogenated castor oil.

Further mention is made of the oils of the group consisting of isononyl isononanoate, stearyl octanoate, isopropyl palmitate, isopropyl myristate, butyl stearate, hexyl laurate, 2-ethylhexyl palmitate, 2-hexyldecyl laurate, 2-octyldecyl palmitate, 2-octyldodecyl myristate, di(2-ethylhexyl) succinate, diisostearyl malate, 2-octyldodecyl lactate, glyceryl triisostearate or diglyceryl triisostearate, octyldodecyl stearoyl stearate (Ceraphyl), cetearyl isononanoate, diisopropyl adipate, caprylic/capric triglyceride, glyceryl tricaprate/caprylate, isocetyl stearoyl stearate, $C_{12}$-$C_{15}$ alkyl benzoates, pentaerythrityl tetraisostearate, dipentaerythrityl pentaisononanoate, bis-diglyceryl polyacyladipate-2, trimethylolpropane triethylhexanoate, propylene glycol dibenzoate, propylene glycol dioctanoate, and mixture thereof.

Mention is made, as example of volatile silicone oils, of hexamethyldisiloxane, dimethicones with a viscosity of between 0.65 and 5 mm$^2$/s, octamethylcyclotetrasiloxane, heptamethylhexyltrisiloxane, decamethylcyclopentasiloxane, decamethyltetrasiloxane, octamethyltrisiloxane, dodecamethylcyclohexasiloxane, heptamethyloctyltrisiloxane, and their mixtures.

Mention is made, as example of non-volatile silicone oils, of non-volatile polydialkylsiloxanes; polydimethylsiloxanes comprising pendant alkyl, alkoxy or phenyl groups or alkyl, alkoxy or phenyl groups at the end of the silicone chain, which groups have from 2 to 24 carbon atoms; phenylated silicones, such as those of the phenyl trimethicone type, those of the phenylpropyldimethylsiloxysilicate type or those of the trimethylpentaphenyltrisiloxane type; polysiloxanes modified by fatty acids, in particular $C_8$-$C_{20}$ fatty acids, fatty alcohols, in particular $C_8$-$C_{20}$ fatty alcohols, or polyoxyalkylenes (in particular polyoxyethylene and/or polyoxypropylene); aminated polysiloxanes; polysiloxanes comprising a hydroxyl group; and their mixtures.

Mention is made, as fluorosilicone oils, of fluorinated polysiloxanes comprising a pendant fluorinated group or a fluorinated group at the end of the silicone chain having from 1 to 12 carbon atoms, all or a portion of the hydrogens of which are replaced by fluorine atoms, such as perfluorononyl dimethicone, and their mixtures.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained. In some cases, the one or more emulsifiers may be selected from the group consisting polyglycerol esters of fatty acids, alkyl polyglycosides, polysorbates, amino acid emulsifiers, and an alkyl amine oxides. Further, in some cases the microemulsion include at least one polyglycerol ester of fatty acids, which has the following formula:

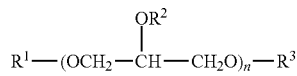

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. Non-limiting examples include glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

In some instances, the microemulsion compositions of the instant disclosure include at least one polyglyceryl fatty acid ester, preferably with a polyglyceryl moiety derived from 4 to 6 glycerins, more preferably 5 or 6 glycerins. The polyglyceryl fatty acid ester may have an HLB value of from 8.0 to 14.0, preferably from 9.0 to 13.5, and more preferably from 10.0 to 13.0. The polyglyceryl fatty acid ester may be chosen from polyglyceryl monolaurate comprising 3 to 6 glycerol units, polyglyceryl mono(iso)stearate comprising 3 to 6 glycerol units, polyglyceryl monooleate comprising 3 to 6 glycerol units, or polyglyceryl dioleate comprising 3 to 6 glycerol units.

The polyglyceryl fatty acid ester may be chosen from a mixture of polyglyceryl fatty acid esters, for example, with a polyglyceryl moiety derived from 3 to 6 glycerins, more preferably 5 or 6 glycerins. The polyglyceryl fatty acid ester raw material may comprises esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount of the polyglyceryl fatty acid ester may range from 0.1 to 25% by weight, from 0.5 to 20% by weight, from 0.5 to 15% by weight, or from 0.5 to 10% by weight. Further, the total amount of polyglyceryl fatty acid ester in a microemulsion composition can be from 0.5 to 8 wt. %, 0.5 to 6 wt. %, 0.5 to 5 wt. %, 1 to 10 wt. %, 1 to 8 wt. %, 1 to 6 wt. %, 1 to 5 wt. %, 2 to 10 wt. %, 2 to 8 wt. %, 2 to 6 wt. %, 2 to 5 wt. %, 3 to 10 wt. %, 3 to 8 wt. %, 3 to 6 wt. %, or 3 to 5 wt. %.

The one or more emulsifiers may include one or more amino acid emulsifiers. In particular, the amino acid emulsifiers include those derived from taurate, glutamate, alanin or alaninate, sarcosinate and aspartate. Amino acid emulsifiers typically have the following structure:

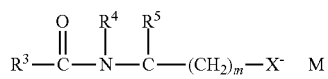

wherein $R^3$ is a saturated or unsaturated, straight or branched alkyl chain with 7 to 17 C atoms, $R^4$ is H or a methyl, $R^5$ is H, COO$^-$M$^+$, CH$^2$COO$^-$M or COOH, m is 0 to 2, X is COO$^-$ or SO$_3^-$ and M is independently H, sodium, potassium or ammonium. In some instances, $R^3$ is a saturated or unsaturated, straight or branched alkyl chain with 9 to 17 C atoms, or 9 to 13 C atoms, $R^4$ is H or a methyl, $R^5$ is H, COO"M$^+$, CH$_2$COO'M or COOH, m is 0 to 2, X is COO" or SO$_3$" and M is independently H, sodium or potassium Non-limiting examples of amino acid emulsifiers include potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine palmitoyl glycine, sodium lauroyl glycine, sodium cocoyl glycine, sodium myristoyl glycine, potassium lauroyl glycine, potassium cocoyl glycine, potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof.

Particular mention may be made of potassium lauroyl sarcosinate, potassium cocoyl sarcosinate, sodium cocoyl sarcosinate, sodium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

Further, non-limiting examples of emulsifiers that may be mentioned include nonionic emulsifiers such as oxyalkylenated (more particularly polyoxyethylenated); oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15 lauryl dimethicone crosspolymer, PEG-15 laurylpolydimethylsiloxyethyl crosspolymer.

In some instances, the microemulsion compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

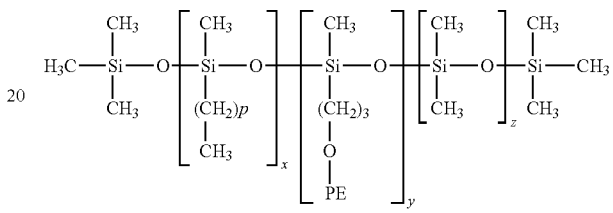

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

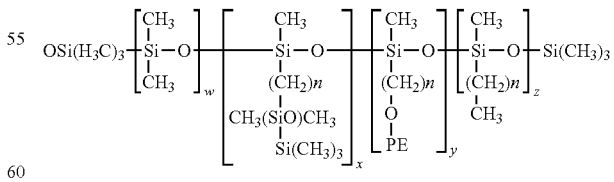

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some cases the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15 Lauryl Dimethicone Crosspolymer; and PEG-15 Laurylpolydimethylsiloxyethyl Crosspolymer.

Cosmetically Acceptable Carrier

The water and or the glycols in the microemulsion compositions typically form part or all of a cosmetically acceptable carrier. The cosmetically acceptable carrier can include, for example, glycerin, $C_{1-4}$ alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

UV Filters

UV filters are well known in the art for their use in stopping UV radiation and may optionally be included in the microemulsion compositions. For example, the UV filter may be one or more organic UV filters and/or one or more inorganic UV filters. Non-limiting examples of UV filters include:
i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]- and mixtures thereof.
ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
iii. Inorganic UV filters such as titanium oxide and zinc oxide, iron oxide, zirconium oxide and cerium oxide; and
iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

Implementation of the present disclosure is provided by way of the following examples. The examples serve to illustrate the technology without being limiting in nature.

EXAMPLES

Thirteen formulations were prepared using the components and amounts shown in the table below.

| Function | US INCI Name | Amount (wt. %) |
|---|---|---|
| Active | Polydatin | 0-1.5 |
| | Niacinamide (Vitamin B3) | 1.5-2.5 |
| | Baicalin | 0-0.5 |
| Emulsifiers | Polyglycerol ester of fatty acid | 3.5-5.0 |
| | Amino Acid Emulsifier | 0.1 |
| Oil | Ester Oil (obtained from a $C_{12}$-$C_{22}$ linear fatty acid and a $C_{6-24}$ linear or branched alcohol) | 1.5-3.0 |
| Carrier | Glycols | 20.5-24.5 |
| | Water | q.s. |

Details of the thirteen formulations are presented in the table below.

| No | B3 | Polydatin | Baicalin | Emulsifiers | Oil | BG | PG/Oil Ratio | Micro-Emulsion | Clear | Stable |
|---|---|---|---|---|---|---|---|---|---|---|
| Inventive Formulations ||||||||||
| 1 | 2.5 | 1.5 | 0.5 | 4.1 | 2 | 20 | 2.0 | Yes | Yes | Yes |
| 2 | 1.5 | 1 | 0.5 | 5.1 | 3 | 22.5 | 1.7 | Yes | Yes | Yes |
| 3 | 2 | 1.5 | 0.5 | 5.1 | 2 | 24 | 2.5 | Yes | Yes | Yes |
| 4 | 2 | 1 | 0.5 | 4.6 | 2 | 23 | 2.3 | Yes | Yes | Yes |
| 5 | 2.5 | 1 | 0.5 | 5.1 | 2.5 | 24 | 2.0 | Yes | Yes | Yes |
| 6 | 1.5 | 1 | 0.5 | 5.1 | 2.5 | 22 | 2.0 | Yes | Yes | Yes |
| 7 | 2.5 | 1 | 0.5 | 4.1 | 2 | 23 | 2.0 | Yes | Yes | Yes |
| 8 | 2.5 | 1 | 0.5 | 5.1 | 2.5 | 21 | 2.0 | Yes | Yes | Yes |
| 9 | 2.5 | 0.5 | 0.5 | 3.6 | 2 | 25 | 1.8 | Yes | Yes | Yes |
| 10 | 2.5 | 0.5 | 0.5 | 3.6 | 1.5 | 21 | 2.3 | Yes | Yes | Yes |
| 11 | 2.5 | 1.5 | 0.5 | 4.1 | 2 | 20 | 2.0 | Yes | Yes | Yes |
| Control Formulations ||||||||||
| 12 | 2.5 | 0 | 0.5 | 4.1 | 2 | 20 | 2.0 | No | No | No |
| 13 | 2.5 | 0 | 0 | 4.1 | 2 | 20 | 2.0 | No | No | No |
| Non-Microemulsion Forming Formulations ||||||||||
| 14 | 2.5 | 1 | 0.5 | 4.6 | 1 | 20 | 4.5 | No | No | No |
| 15 | 2.5 | 1 | 0.5 | 4.1 | 1 | 24 | 4 | No | No | No |

-continued

| No | B3 | Polydatin | Baicalin | Emulsifiers | Oil | BG | PG/Oil Ratio | Micro-Emulsion | Clear | Stable |
|----|-----|-----|-----|-----|-----|----|-----|-----|-----|-----|
| 16 | 1.5 | 1 | 0.5 | 4.1 | 1 | 25 | 4 | No | No | No |
| 17 | 1.5 | 1 | 0.5 | 4.6 | 3 | 24 | 1.5 | No | No | No |
| 18 | 2 | 1 | 0.5 | 4.6 | 3 | 24 | 1.5 | No | No | No |
| 19 | 2.5 | 1 | 0.5 | 4.1 | 1 | 25 | 4 | No | No | No |
| 20 | 2 | 1 | 0.5 | 4.1 | 3 | 24 | 1.3 | No | No | No |
| 21 | 2 | 1 | 0.5 | 5.1 | 1.5 | 24 | 3.3 | No | No | No |
| 22 | 1.5 | 1 | 0.5 | 4.1 | 1.5 | 21 | 2.7 | No | No | No |
| 23 | 2.5 | 1 | 0.5 | 4.1 | 1.5 | 20 | 2.7 | No | No | No |
| 24 | 1.5 | 1 | 0.5 | 5.1 | 1.5 | 20 | 3.3 | No | No | No |
| 25 | 1.5 | 1 | 0.5 | 4.1 | 1 | 20 | 4 | No | No | No |
| 26 | 2 | 1 | 0.5 | 4.1 | 3 | 20 | 1.3 | No | No | No |
| 27 | 1.5 | 1.5 | 0.5 | 4.6 | 3 | 22 | 1.5 | No | No | No |
| 28 | 2.5 | 1.5 | 0.5 | 4.6 | 3 | 24 | 1.5 | No | No | No |
| 29 | 2.5 | 1.5 | 0.5 | 4.1 | 3 | 20 | 1.3 | No | No | No |
| 30 | 2.5 | 1.5 | 0.5 | 4.1 | 3 | 21 | 1.3 | No | No | No |
| 31 | 2 | 1.5 | 0.5 | 4.6 | 3 | 20 | 1.5 | No | No | No |
| 32 | 1.5 | 1.5 | 0.5 | 4.1 | 3 | 23 | 1.3 | No | No | No |
| 33 | 2.5 | 1.5 | 0.5 | 4.1 | 1 | 22 | 4 | No | No | No |
| 34 | 1.5 | 1.5 | 0.5 | 4.6 | 1 | 24 | 4.5 | No | No | No |
| 35 | 1.5 | 1.5 | 0.5 | 4.1 | 1.5 | 21 | 2.7 | No | No | No |
| 36 | 2.5 | 1.5 | 0.5 | 5.1 | 2.5 | 24 | 2 | No | No | No |
| 37 | 2.5 | 1.5 | 0.5 | 5.1 | 1.5 | 25 | 3.3 | No | No | No |
| 38 | 2 | 1.5 | 0.5 | 5.1 | 1.5 | 20 | 3.3 | No | No | No |
| 39 | 2.5 | 1.5 | 0.5 | 5.1 | 1.5 | 23 | 3.3 | No | No | No |

As shown by the data in the table above, when the surfactant/oil ratio is between about 1.7 to about 2.5, the resulting microemulsion is stable. When the surfactant/oil ratio is outside this range, a stable microemulsion does not form (typically phase separation occurs).

The data in the table also show that if polydatin is omitted form the formulations (Formulations 12 and 13) the compositions do not form a microemulsion, are not clear (T~50%), and are unstable (phase separate). However, when polydatin is included, a microemulsion composition forms that is clear and stable. This shows that polydatin surprisingly improves transparency, contributes to microemulsion composition formation, and stabilizes the formulations.

The inventive formulations improved the solubility of polydatin up to 1.5%, which is more than 150 times higher than the solubility of polydatin in water alone. Formulations 11 and 12 are identical except that formulation 11 includes polydatin and Formulation 12 does not. Both formulations include baicalin. If baicalin is used without polydatin, a microemulsion does not form, the composition is not clear, and the composition is not stable (Formulation 12). However, when polydatin is added, a microemulsion forms, the composition is clear, and the composition is stable (Formulation 11). Thus, in addition to polydatin, the microemulsion composition of the instant disclosure are effective for incorporating baicalin into cosmetic and/or pharmaceutical compositions.

In the context of the instant disclosure, the term "microemulsion" refers to a suspension or mixture of tiny droplets of one liquid (oil component) in a second liquid (aqueous component). A microemulsion composition is clear and thermodynamically stable; and is a isotropic liquid mixture of oil, water and surfactant, frequently in combination with a co-surfactant.

The term "full spectrum photo protection" refers to protection against at least UV radiation and to protection against visible light and/or IR ration.

The difference between "broad spectrum photo protection" and "full spectrum photo protection" is that "full spectrum photo protection" necessarily includes protection against UV radiation in addition to protection against visible light and/or IR radiation. "Broad spectrum photo protection," however, includes protection of visible light and/or IR radiation but not necessarily protection against UV radiation. The addition of UV filters to a composition providing "broad spectrum photo protection" would transform the composition into one that provides "full spectrum photo protection" (because the addition of the UV filters allows the composition to provide protection against UV radiation and visible light and/or IR radiation.

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about," if desired to impart the meaning above, or recited without the term, regardless of whether the term "about" is specifically set forth (or is absent) in conjunction with any particular value in the specification.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A microemulsion composition comprising:
   (a) 0.1 to 5 wt. % of polydatin;
   (b) optionally, 0.1 to 10 wt. % of niacinamide;
   (c) optionally, 0.1 to 3 wt. % of baicalin;
   (d) at least 0.5 wt. % of one or more oils;

(e) water; and (f) up to 10 wt. % of one or more emulsifiers, wherein the weight ratio of the total amount of the one or more emulsifiers to the total amount of the one or more oils is 1.7 to 2.5 (one or more emulsifiers/one or more oils).

2. The microemulsion composition of claim 1, wherein the one or more emulsifiers are selected from the group consisting polygylcerol esters of fatty acids, alkyl polyglycosides, polysorbates, amino acid emulsifiers, and an alkyl amine oxides.

3. The microemulsion composition of claim 2, wherein the one or more emulsifiers comprises a polyglycerol ester of fatty acids.

4. The microemulsion composition of claim 3, wherein the polyglycerol ester of fatty acids is a nonionic polyglycerol ester of fatty acids selected from the group consisting of polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

5. The microemulsion composition of claim 4, wherein the polyglycerol ester of fatty acids is polyglycerol-5 laurate.

6. The microemulsion composition of claim 2, wherein the one or more emulsifiers comprises an amino acid emulsifier.

7. The microemulsion composition of claim 6, wherein the amino acid emulsifier is selected from the group consisting of potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine palmitoyl glycine, sodium lauroyl glycine, sodium cocoyl glycine, sodium myristoyl glycine, potassium lauroyl glycine, potassium cocoyl glycine, potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof.

8. The microemulsion composition of claim 2, wherein the one or amino acid emulsifiers are selected from the group consisting of sodium methyl oleoyl taurate, sodium methyl stearoyl taurate, sodium methyl palmitoyl taurate, sodium methyl myristoyl taurate, sodium methyl lauroyl taurate, sodium methyl cocoyl taurate, and mixtures thereof.

9. The microemulsion composition of claim 8, comprising sodium methyl stearoyl taurate.

10. The microemulsion composition of claim 1 comprising 50 to 85 wt. % of the water of (e).

11. The microemulsion composition of claim 1, further comprising:

(g) 5 to 40 wt. % of one or more glycols.

12. The microemulsion composition of claim 1, wherein the one or more oils comprises an ester oil obtained from a $C_{12}$-$C_{22}$ linear fatty acid and a $C_{6-24}$ linear or branched alcohol.

13. A microemulsion composition of claim 1 that is clear.

14. A microemulsion composition comprising:

(a) 0.1 to 5 wt. % of polydatin;

(b) 0.1 to 10 wt. % of niacinamide;

(c) 0.1 to 3 wt. % of baicalin;

(d) at least 0.5 wt. % of one or more oils;

(e) 50 to 85 wt. % of water;

(f) up to 10 wt. % of one or more emulsifiers, wherein the one or more emulsifiers include a polyglycerol ester of fatty acids; and wherein the weight ratio of the total amount of the one or more emulsifiers to the total amount of the one or more oils (one or more emulsifiers/one or more oils) is 1.7 to 2.5; and (g) 5 to 40 wt. % of one or more glycols.

15. A method for improving the appearance of skin or method for enhancing the skin penetration of polydatin comprising applying a microemulsion composition of claim 1 to the skin.

16. A method for enhancing the solubility of polydatin comprising incorporating polydatin into a microemulsion composition such that the microemulsion composition comprises:

(a) 0.1 to 5 wt. % of polydatin;

(b) optionally, 0.1 to 10 wt. % of niacinamide;

(c) optionally, 0.1 to 3 wt. % of baicalin;

(d) 0.5 to 15 wt. % of one or more oils;

(e) water; and (f) 0.5 to 10 wt. % of one or more emulsifiers, wherein the weight ratio of the total amount of the one or more emulsifiers to the total amount of the one or more oils (one or more emulsifiers/one or more oils) is 1.7 to 2.5.

* * * * *